(12) United States Patent
Nakajima et al.

(10) Patent No.: US 8,682,429 B2
(45) Date of Patent: Mar. 25, 2014

(54) NERVE STIMULATION APPARATUS

(75) Inventors: Keiichiro Nakajima, Tokyo (JP); Hiroki Hibino, Tokyo (JP)

(73) Assignee: Olympus Corporation, Tokyo (JP)

( * ) Notice: Subject to any disclaimer, the term of this patent is extended or adjusted under 35 U.S.C. 154(b) by 130 days.

(21) Appl. No.: 13/034,374

(22) Filed: Feb. 24, 2011

(65) Prior Publication Data

US 2012/0053650 A1 Mar. 1, 2012

(30) Foreign Application Priority Data

Aug. 31, 2010 (JP) ................................. 2010-194141

(51) Int. Cl.
*A61N 1/00* (2006.01)

(52) U.S. Cl.
USPC .............................................................. 607/9

(58) Field of Classification Search
USPC .......................................................... 607/9, 2
See application file for complete search history.

(56) References Cited

U.S. PATENT DOCUMENTS

2007/0250124 A1* 10/2007 Burnes et al. ...................... 607/9
2008/0132966 A1* 6/2008 Levin et al. ...................... 607/17

FOREIGN PATENT DOCUMENTS

JP 2008-532638 8/2008
JP 4252833 1/2009

OTHER PUBLICATIONS

Abstract only of International Publication No. WO 2006/098996, dated Sep. 21, 2006.
Abstract only of Japanese Patent Publication No. 2004-290536, dated Oct. 21, 2004.

* cited by examiner

*Primary Examiner* — Christopher D Koharski
*Assistant Examiner* — Philip Edwards
(74) *Attorney, Agent, or Firm* — Scully, Scott, Murphy & Presser, P.C.

(57) ABSTRACT

A nerve stimulation apparatus performs nerve stimulation of a required level while reducing the adverse effect on the heart and on the detection of a cardiac event. Provided is a nerve stimulation apparatus that includes a stimulation signal output unit that outputs a nerve stimulation signal; a cardiac event detector that detects a cardiac event; and a controller that controls the stimulation signal output unit so as to output a nerve stimulation signal having a smaller intensity in a non-refractory period than that in a cardiac refractory period that is obtained on the basis of the cardiac event detected by the cardiac event detector.

9 Claims, 4 Drawing Sheets

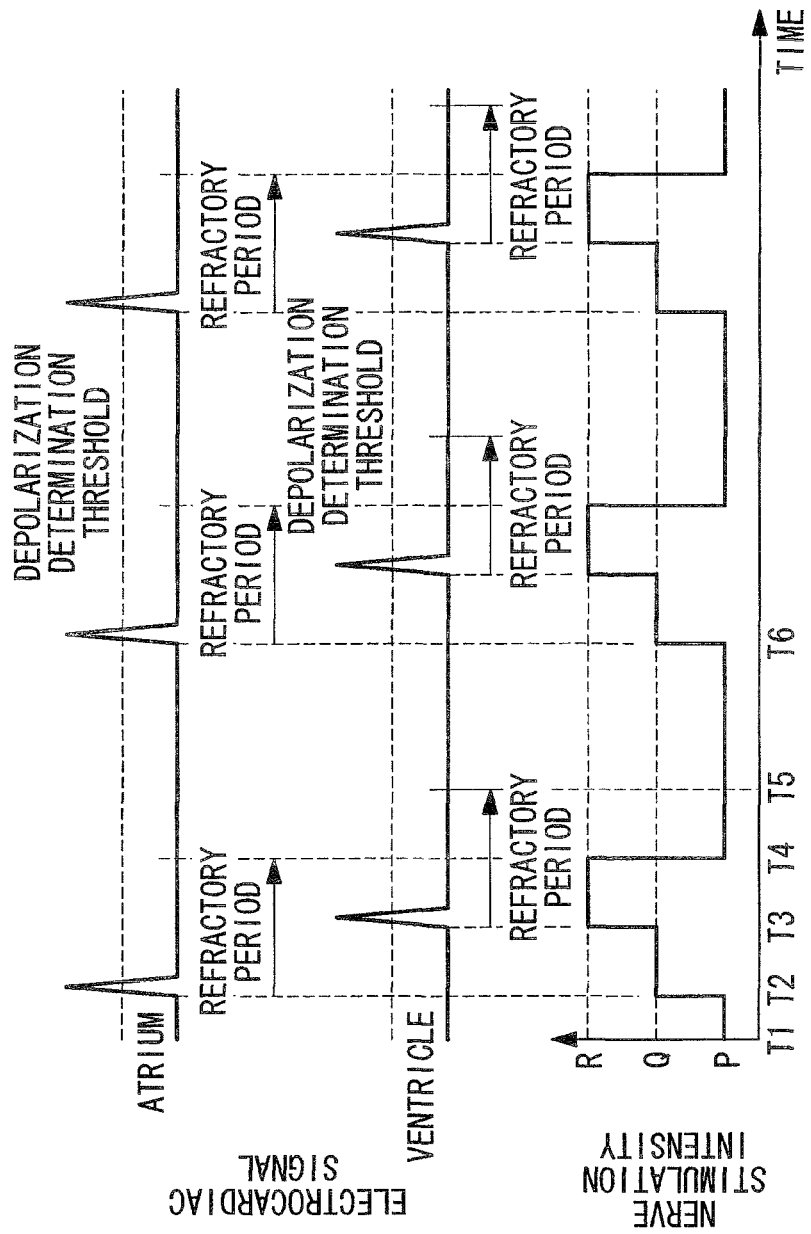

NERVE STIMULATION APPARATUS

BACKGROUND OF THE INVENTION

1. Field of the Invention

The present invention relates to a nerve stimulation apparatus.

This application is based on Japanese Patent Application No. 2010-194141, the content of which is incorporated herein by reference.

2. Description of Related Art

There is a known method in the related art in which cardiac resynchronization combination therapy is performed by stimulating a nerve found in the vicinity of the heart (for example, see Japanese Translation of PCT International Application, Publication No. 2008-532638). In this method, when the nerve found in the vicinity of the heart is stimulated, it has been proposed to provide nerve stimulation in a cardiac refractory period so as not to stimulate the heart itself.

BRIEF SUMMARY OF THE INVENTION

However, if the stimulation period of the nerve is limited to the cardiac refractory period, sufficient nerve stimulation may not be possible.

Therefore, the present invention employs the following solutions.

One aspect of the present invention provides a nerve stimulation apparatus including: a stimulation signal output unit that outputs a nerve stimulation signal; a cardiac event detector that detects a cardiac event; and a controller that controls the stimulation signal output unit so as to output a nerve stimulation signal having a smaller intensity in a non-refractory period than that in a cardiac refractory period that is obtained on the basis of the cardiac event detected by the cardiac event detector.

If the nerve stimulation signal is a pulse signal, for example, the intensity thereof can be defined by four parameters: the pulse voltage, the pulse duration, the frequency, and the output time. Each parameter may be varied individually to vary the intensity, or two or more parameters may be combined to vary the intensity.

In the above-described invention, the intensity of the nerve stimulation signal may be equal to the energy per pulse signal that is output from the stimulation signal output unit.

In the above-described invention, the intensity of the nerve stimulation signal may be equal to the energy per unit time of the nerve stimulation signal that is output from the stimulation signal output unit.

In the above-described invention, the intensity of the nerve stimulation signal may be equal to the total energy of the nerve stimulation signal that is output from the stimulation signal output unit.

In the above-described invention, the nerve stimulation signal that is output from the stimulation signal output unit in the non-refractory period may have an intensity that does not stimulate the heart.

In the above-described invention, the nerve stimulation signal that is output from the stimulation signal output unit in the non-refractory period may have an intensity that does not stimulate the atrium.

In the above-described invention, the nerve stimulation signal that is output from the stimulation signal output unit in the non-refractory period may have an intensity that does not stimulate the ventricle.

In the above-described invention, the controller may control the stimulation signal output unit such that the nerve stimulation signal that is output from the stimulation signal output unit in the non-refractory period has an intensity upper limit that does not stimulate the heart, and such that the nerve stimulation signal that is output from the stimulation signal output unit in the refractory period has an intensity larger than the upper limit.

In the above-described invention, the controller may obtain a refractory period of the ventricle and a refractory period of the atrium as the cardiac refractory period and control the stimulation signal output unit such that the nerve stimulation signal that is output from the stimulation signal output unit in the non-refractory period of the atrium has an intensity upper limit that does not stimulate the atrium, the nerve stimulation signal that is output from the stimulation signal output unit in the refractory period of the atrium and in the non-refractory period of the ventricle has an intensity upper limit that does not stimulate the ventricle, and the nerve stimulation signal that is output from the stimulation signal output unit in the refractory period of the atrium and in the refractory period of the ventricle has a larger intensity than the intensity upper limit that does not stimulate the ventricle.

BRIEF DESCRIPTION OF THE SEVERAL VIEWS OF THE DRAWINGS

FIG. 4 is a time chart showing the relationship between an electrocardiac signal and stimulation intensity in a modification of the nerve stimulation apparatus in FIG. 1, in which an upper limit of a nerve stimulation intensity in a non-refractory period is set for each of the atrium and the ventricle.

DETAILED DESCRIPTION OF THE INVENTION

A nerve stimulation apparatus 1 according to an embodiment of the present invention will be described below, with reference to the drawings.

Figure 1:
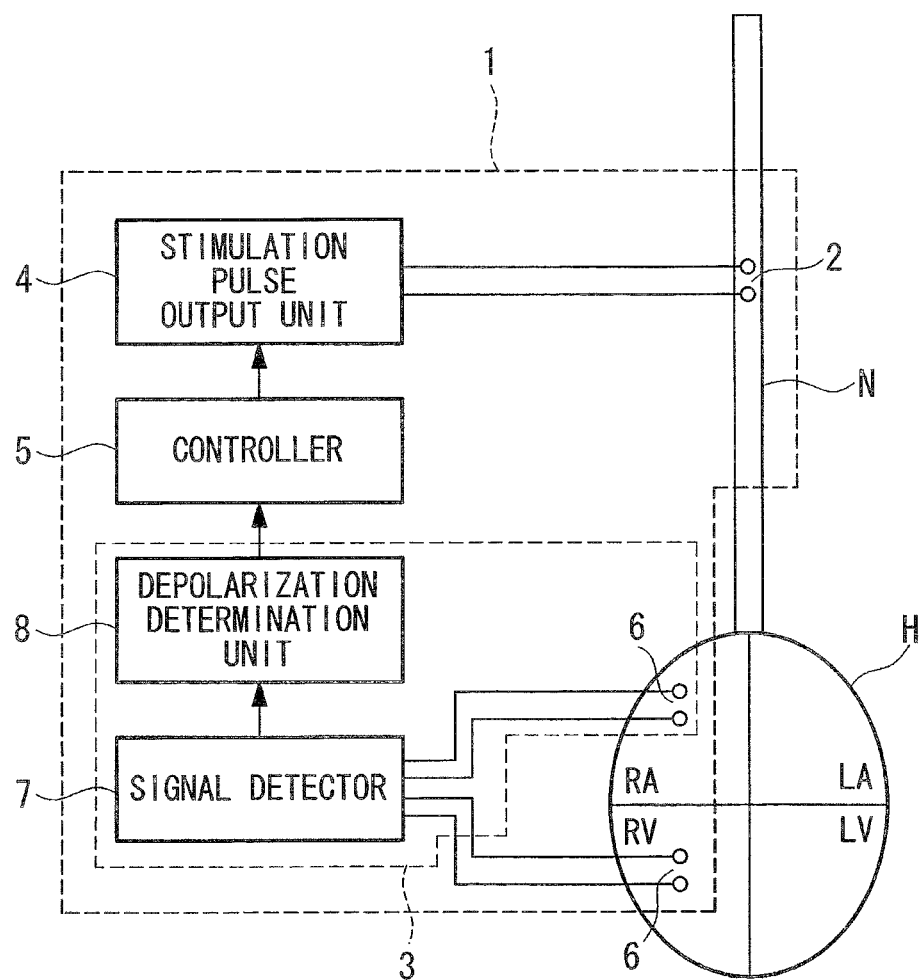
FIG. 1 is a diagram showing the overall configuration of a nerve stimulation apparatus according to an embodiment of the present invention.

As shown in FIG. 1, the nerve stimulation apparatus 1 according to this embodiment has electrodes 2 attached to a nerve N in the vicinity of the heart H, such as the vagus nerve etc., a cardiac event detector 3 that detects an event in the heart H (cardiac event), a stimulation pulse output unit 4 that outputs a stimulation pulse to the nerve N through the electrode 2, and a controller 5 that controls the stimulation pulse output unit 4 on the basis of the cardiac event detected with the cardiac event detector 3.

The cardiac event detector 3 has two or more indwelling detection electrodes 6 that are in contact with each of parts of the heart H (for example, in the example shown in FIG. 1, the right atrium RA and the right ventricle RV), a signal detector 7 that detects an electrocardiac signal through the two or more detection electrodes 6, and a depolarization determination unit 8 that determines that, when the signal detected with the signal detector 7 exceeds a predetermined threshold, the heart H is undergoing a depolarization at that point. In the figure, reference sign LA is the left atrium and reference sign LV is the left ventricle.

The detection electrodes 6 consist of a cathode (Tip electrode) and an anode (Ring electrode), and the respective electrodes are connected to conductive wires. The conductive wires are coated with insulation so as not to cause a short circuit between the cathode and the anode. These insulation-coated wires are further coated with insulation after two wires have been bound together (in the figure, the insulating coating is omitted). The signal detector 7 detects an electric potential difference formed between the cathode and the anode of the detection electrodes 6 as an electrocardiac signal.

The stimulation pulse output unit 4 generates a stimulation pulse train for electrically stimulating the nerve N and supplies the nerve N with the generated stimulation pulse train via the electrodes 2. Parameters that determine the intensity of the stimulation pulse train include the pulse voltage, the pulse duration, the pulse frequency (frequency), and the output time.

The electrodes 2 also consist of a cathode (Tip electrode) and an anode (Ring electrode), and the respective electrodes are connected to conductive wires. The conductive wires are coated with insulation so as not to cause a short circuit between the cathode and the anode. These insulation-coated wires are further coated with insulation after two wires have been bound together (in the figure, the insulating coating is omitted). The stimulation pulse output unit 4 outputs the stimulation pulse train, which is to be supplied to the nerve N, between the cathode and the anode of the electrodes 2.

When the depolarization determination unit 8 determines that depolarization of the heart H has occurred, it outputs to the controller 5 a signal indicating that the depolarization has occurred.

The controller 5 has a timer (not shown). The controller 5 resets the timer and starts measuring the elapsed time every time the signal indicating the occurrence of depolarization is received from the depolarization determination unit 8.

A refractory period of the heart H of 150 ms, for example, is set in the controller 5, and the period of 150 ms starting from the point at which the signal indicating the occurrence of depolarization is received from the depolarization determination unit 8 is determined as the refractory period. If the elapsed time measured by the timer is in the refractory period, then the controller 5 causes the stimulation pulse output unit 4 to output the stimulation pulse based on predetermined parameters, and if the elapsed time is in the non-refractory period, then the controller 5 causes the stimulation pulse output unit 4 to output a weaker stimulation pulse than the stimulation pulse output in the refractory period. The non-refractory period is considerably longer than the refractory period.

An example of the intensity of the stimulation pulse is shown in Table 1.

TABLE 1

| Variable parameter | Refractory period | Non-refractory period |
|---|---|---|
| Pulse voltage | pulse voltage 6 V pulse duration 2 ms/ pulse frequency 60 Hz/ output time 100 ms | same as the left cell except 3 V pulse voltage |
| Pulse duration | pulse duration 2 ms pulse voltage 6 V/ pulse frequency 60 Hz/ output time 100 ms | same as the left cell except 1 ms pulse duration |
| Pulse frequency | pulse frequency 60 Hz pulse voltage 6 V/ pulse duration 2 ms/ output time 100 ms | same as the left cell except 30 Hz pulse frequency |
| Output time | output time 100 ms | same as the |

TABLE 1-continued

| Variable parameter | Refractory period | Non-refractory period |
|---|---|---|
| | pulse voltage 6 V/ pulse duration 2 ms/ pulse frequency 60 Hz | left cell except 50 ms output time |

A first intensity of the stimulation pulse in the refractory period of the heart H is set to an intensity sufficiently larger than a second intensity in the non-refractory period, and the second intensity is set so as not to stimulate the heart H or to affect the detection of a cardiac event.

The operation and effects of the thus-configured nerve stimulation apparatus 1 according to this embodiment will be described below.

According to the nerve stimulation apparatus 1 of this embodiment, the signal detector 7 detects electrocardiac signals appear between the detection electrodes 6 of the cardiac event detector 3 that indwell in the heart H; when the detected electrocardiac signal exceeds a predetermined threshold, the depolarization determination unit 8 determines that the depolarization of the heart H has occurred, and the signal indicating so is sent to the controller 5.

Figure 2:
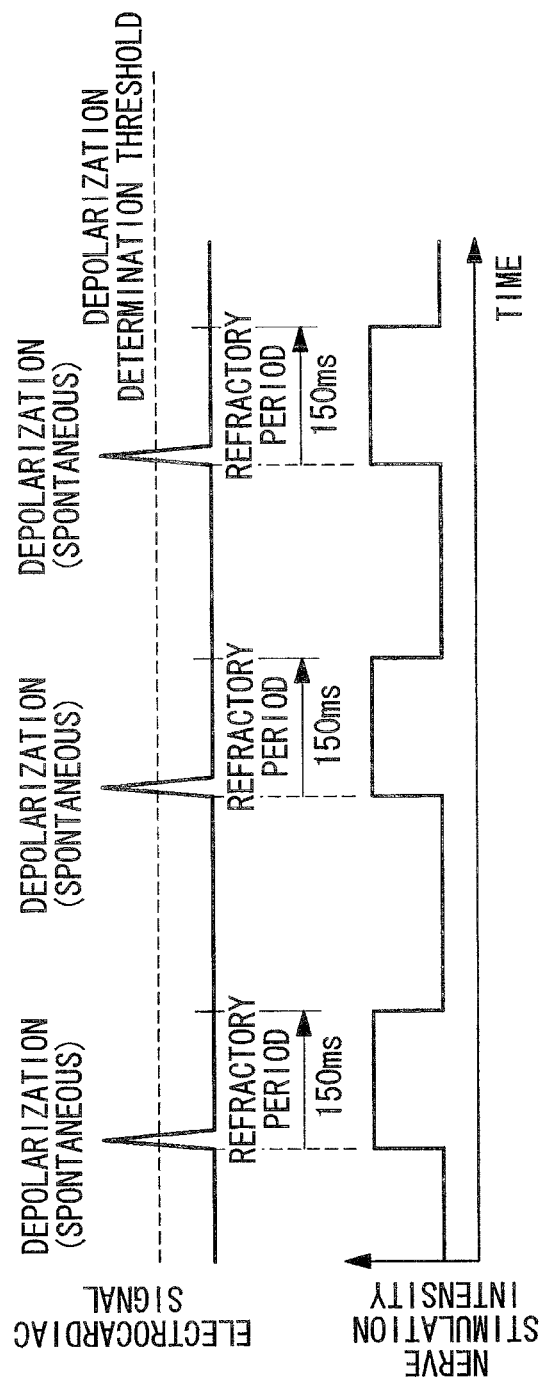
FIG. 2 is a time chart showing the relationship between an electrocardiac signal and stimulation intensity provided by the nerve stimulation apparatus in FIG. 1.

Upon receiving the signal indicating that the depolarization has occurred, as shown in FIG. 2, the controller 5 resets the timer and starts measuring the elapsed time, and causes the stimulation pulse output unit 4 to output the first-intensity stimulation pulse in the refractory period until the period of 150 ms, that is the refractory period, has elapsed. After the time period of 150 ms measured by the timer has elapsed, the controller 5 causes the stimulation pulse output unit 4 to output the second-intensity stimulation pulse in the non-refractory period.

The second-intensity stimulation pulse does not affect the heart H and the detection of a cardiac event, and it is possible to continuously provide sufficient stimulation to the nerve N for a long duration in the non-refractory period. In addition, because the first intensity is set sufficiently higher than the second intensity, it is possible to provide the nerve N with a higher nerve stimulation than the second-intensity stimulation pulse.

In the refractory period, even if a high-intensity stimulation pulse is provided, the heart H is not adversely affected, and in addition, even if the detection of a cardiac event is affected, this effect can be removed easily. Therefore, according to the nerve stimulation apparatus 1 of this embodiment, an advantage is afforded in that it is possible to provide sufficient nerve stimulation while reducing an adverse effect on the heart H.

In this embodiment, a time period of 150 ms that corresponds to the refractory period of the heart H is set, and a single intensity of the stimulation pulse is set for each of the refractory period and the non-refractory period. Instead of this, however, a plurality of intensities of the stimulation pulse may be set for each of the refractory period and the non-refractory period.

The intensity of the stimulation pulse is set according to the voltage value of the pulse, the pulse duration, the pulse frequency (frequency), and the output time. Instead of this, however, the intensity of the stimulation pulse may be defined by the energy per stimulation pulse. In other words, since the energy per stimulation pulse is proportional to the product of the pulse voltage and the pulse duration, the energy may be set as shown in Table 2. By doing so, the energy per pulse signal can be defined by the product of the pulse voltage and the pulse duration. Furthermore, by considering the intensity of the nerve stimulation signal in terms of the energy, it is possible to estimate the influence on the heart more accurately, and it is possible to perform the nerve stimulation while reducing the adverse effect on the heart.

TABLE 2

|  | Pulse voltage | Pulse duration | Energy per pulse |
|---|---|---|---|
| Refractory period | 6 V | 2 ms | 12 |
| Non-refractory period | 8 V | 1 ms | 8 |

In addition, instead of the energy per pulse, the intensity of the stimulation pulse may be defined by the energy per unit time. In other words, since the energy per unit time is proportional to the product of the pulse voltage, the pulse duration, and the pulse frequency, the energy may be set as shown in Table 3. By doing so, the energy per unit time of the nerve stimulation signal can be defined by the product of the pulse voltage, the pulse duration, and the frequency. Furthermore, by considering the intensity of nerve stimulation signal in terms of the energy per unit time, it is possible to estimate the influence on the heart more accurately, and it is possible to perform the nerve stimulation while reducing the adverse effect on the heart.

TABLE 3

|  | Pulse voltage | Pulse duration | Pulse frequency | Energy per unit time |
|---|---|---|---|---|
| Refractory period | 6 V | 2 ms | 50 Hz | 600 |
| Non-refractory period | 4 V | 1 ms | 30 Hz | 120 |

Furthermore, instead of the energy per unit time, the intensity of the stimulation pulse may be defined by the sum of the stimulation energy provided on the vagus nerve. In other words, since the sum of the stimulation energy is proportional to the product of the pulse voltage, the pulse duration, the pulse frequency, and the output time, the energy may be set as shown in Table 4. By doing so, the sum of the energy of the nerve stimulation signal can be defined by the product of the pulse voltage, the pulse duration, the frequency, and the output time. By considering the intensity of nerve stimulation signal in terms of the sum of the energy imparted to the nerve, it is possible to estimate the influence on the heart more accurately, and it is possible to perform the nerve stimulation while reducing the adverse effect on the heart.

TABLE 4

|  | Pulse voltage | Pulse duration | Pulse frequency | Output time | Sum stimulation energy |
|---|---|---|---|---|---|
| Refractory period | 6 V | 2 ms | 50 Hz | 100 ms | 6000 |
| Non-refractory period | 4 V | 1 ms | 30 Hz | 200 ms | 3600 |

In this embodiment, the intensity of the nerve stimulation pulse that is output to the nerve in the non-refractory period of the heart H is set at a level that does not stimulate the heart H. By doing so, even in the non-refractory period, it is possible to output the nerve stimulation signal so as not to stimulate the heart, and it is possible to perform sufficient nerve stimulation while reducing the adverse effect on the heart. Instead of this, however, the intensity may be set to a level that does not stimulate the atria RA and LA, or to a level that does not stimulate the ventricles RV and LV.

As shown in FIG. 1, since the parts for performing nerve stimulation tend to be closer to the atria RA and LA than the ventricles RV and LV, by setting the intensity to a level that does not stimulate the atria RA and LA, it is possible to perform nerve stimulation while reducing the adverse effect on the heart H. In addition, since the adverse effect on the heart H caused by the stimulation of the ventricles RV and LV is worse than that caused by the stimulation of the atria RA and LA, by setting the intensity to a level that does not stimulate the ventricles RV and LV, it is possible to prevent the stimulation having a large adverse effect on the heart H.

It is preferable that the stimulation pulse that is output to the nerve N in the non-refractory period of the heart H be set to an upper limit that does not adversely affect the heart H.

Here, the controller 5 may control the stimulation signal output unit 4 such that the nerve stimulation signal that is output from the stimulation signal output unit 4 in the non-refractory period has an intensity upper limit that does not stimulate the heart H, and such that the nerve stimulation signal that is output from the stimulation signal output unit 4 in the refractory period has an intensity larger than the upper limit. By doing so, in the non-refractory period, it is possible to perform the maximum nerve stimulation while reducing the adverse effect on the heart H. Even in the refractory period, it is possible to perform the nerve stimulation with a larger intensity than that in the non-refractory period, while reducing the adverse effect on the heart H.

In addition, the controller 5 may obtain a refractory period of the ventricle RV and LV and a refractory period of the atrium RA and LA as the cardiac refractory period of the heart H and control the stimulation signal output unit 4 such that the nerve stimulation signal that is output from the stimulation signal output unit 4 in the non-refractory period of the atrium RA and LA has an intensity upper limit that does not stimulate the atrium RA and LA, the nerve stimulation signal that is output from the stimulation signal output unit 4 in the refractory period of the atrium RA and LA and in the non-refractory period of the ventricle RV and LV has an intensity upper limit that does not stimulate the ventricle RV and LV, and the nerve stimulation signal that is output from the stimulation signal output unit 4 in the refractory period of the atrium RA and LA and in the refractory period of the ventricle RV and LV has a larger intensity than the intensity upper limit that does not stimulate the ventricle RV and LV.

By doing so, in the non-refractory period of each of the atrium RA and LA and the ventricle RV and LV, it is possible to perform the maximum nerve stimulation so as not to adversely affect the atrium RA and LA and the ventricle RV and LV. In addition, in the refractory period of each of the atrium RA and LA and the ventricle RV and LV, it is possible to perform the nerve stimulation with a larger intensity than that in the non-refractory period, while reducing the adverse effect on the atrium RA and LA and the ventricle RV and LV.

An example of a method for setting the upper limit will be described with reference to FIG. 3

Figure 3:
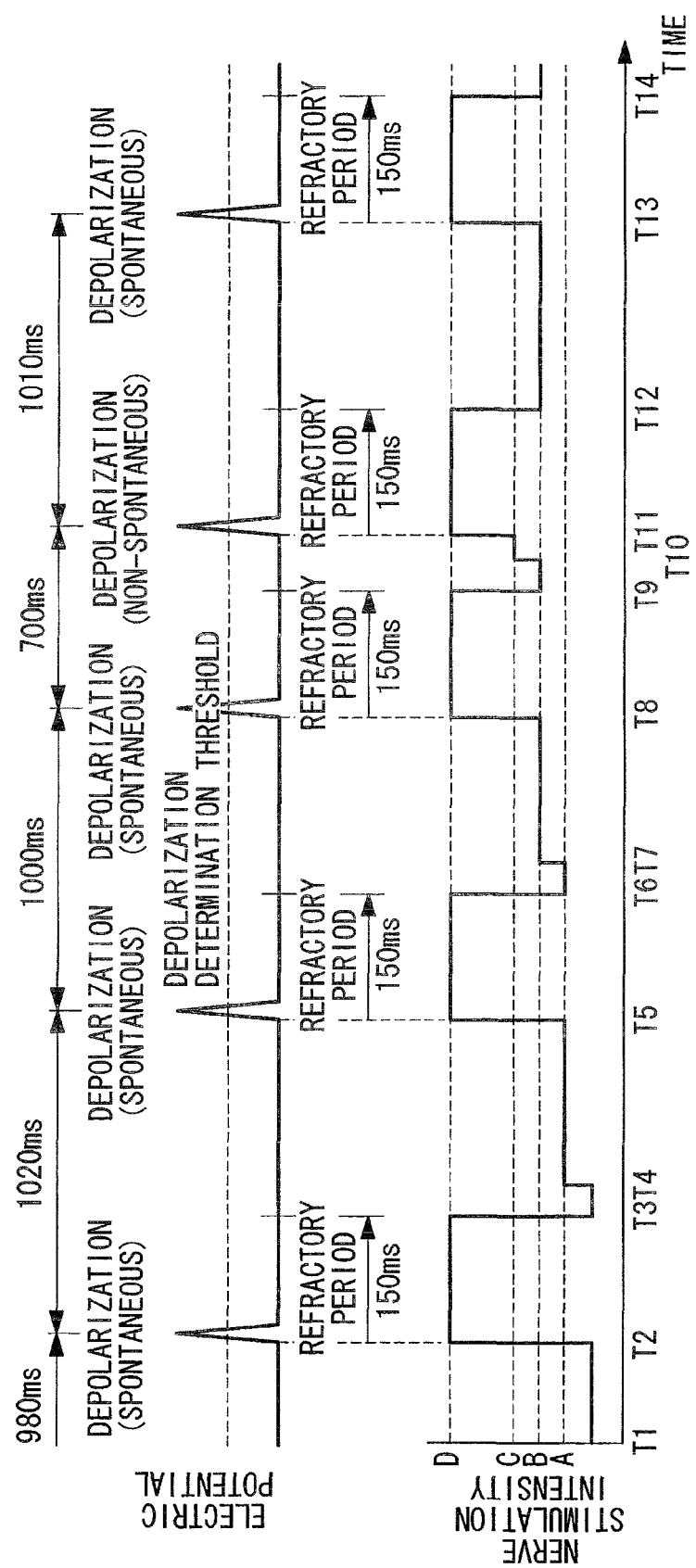
FIG. 3 is a time chart explaining how to decide the upper limit of a nerve stimulation intensity in a non-refractory period in the nerve stimulation apparatus in FIG. 1.

The upper part in FIG. 3 illustrates an example of the electrocardiac signal, and the lower part thereof illustrates the intensities of the nerve stimulation.

The period from T1 to T2 is in the non-refractory period, and the controller 5 sets the stimulation intensity to the previous upper limit (for example, zero).

The period from T2 to T3 is in the refractory period, and the controller 5 sets the stimulation intensity to a pre-set sufficiently large intensity D.

The period from T3 to T4 is in the non-refractory period, and the controller 5 sets the stimulation intensity to the previous upper limit.

The period from T4 to T5 is in the non-refractory period, and the controller 5 sets the stimulation intensity to a slightly larger (for example, about 10% higher) upper limit A than the previous upper limit.

When the depolarization is detected at T5, the controller 5 compares the previous depolarization interval (980 ms) with the depolarization interval at this time (1020 ms) and determines that the depolarization is spontaneous depolarization since the rate of change is smaller than a predetermined value (for example, 10% lower).

The period from T5 to T6 is in the refractory period, and the controller 5 sets the stimulation intensity to the pre-set sufficiently large intensity D.

The period from T6 to T7 is in the non-refractory period, and the controller 5 sets the stimulation intensity to the previous upper limit A.

The period from T7 to T8 is in the non-refractory period, and the controller 5 sets the stimulation intensity to a slightly larger (for example, about 10% higher) upper limit B than the previous upper limit A.

When the depolarization is detected at T8, the controller 5 compares the previous depolarization interval (1020 ms) with the depolarization interval at this time (1000 ms) and determines that the depolarization is spontaneous depolarization since the rate of change is smaller than a predetermined value (for example, 10%).

The period from T8 to T9 is in the refractory period, and the controller 5 sets the stimulation intensity to the pre-set sufficiently large intensity D.

The period from T9 to T10 is in the non-refractory period, and the controller 5 sets the stimulation intensity to the previous upper limit B.

The period from T10 to T11 is in the non-refractory period, and the controller 5 sets the stimulation intensity to a slightly larger upper limit C than the previous upper limit B.

When the depolarization is detected at T11, the controller 5 compares the previous depolarization interval (1000 ms) with the depolarization interval at this time (700 ms), and determines that the depolarization is non-spontaneous depolarization since the rate of change is larger than a predetermined value (for example, 10%).

In other words, the non-spontaneous depolarization is not a natural depolarization but is an unnatural depolarization that is caused as a result of the nerve stimulation; thus it is possible to determine that the heart H is adversely affected. Therefore, the upper limit B one stage earlier than the upper limit C at this time is set as the upper limit of the intensity of the stimulation pulse in the non-refractory period.

The period from T11 to T12 is in the refractory period, and the controller 5 sets the stimulation intensity to the pre-set sufficiently large intensity D.

The period from T12 to T13 is in the non-refractory period, and the controller 5 sets the stimulation intensity to the newly set upper limit B.

The period from T13 to T14 is in the refractory period, and the controller 5 sets the stimulation intensity to the pre-set sufficiently large intensity D.

Here, the periods from T3 to T4, from T6 to T7, and from T9 to T10 are provided in order to prevent a sudden change of the depolarization interval. In addition, the times T4, T7, and T10 may be set to about 60 to 80% of the previous depolarization interval, for example. Thereby, it is possible to obtain the upper limit while preventing a sudden change of the depolarization interval.

In this embodiment, although the refractory period of the heart H is set, the refractory period of the heart H includes the refractory periods of the atria RA and LA and the refractory periods of the ventricles RV and LV, with some partially overlapping periods. The upper limits for the intensities of the nerve stimulation in the respective non-refractory periods differ from each other.

Thus, as shown in FIG. 4, a predetermined 150 ms refractory period may be measured by separately detecting the depolarization of the atria RA and LA and the depolarization of the ventricles RV and LV, and by resetting the timer for the atria RA and LA and the timer for the ventricles RV and LV, at the respective time points.

The period from T1 to T2 is in the non-refractory periods of the ventricles RV and LV and the atria RA and LA, and the smaller upper limit P of the two upper limits is used as the intensity of the stimulation pulse. The period from T2 to T3 is in the atrium refractory period and in the ventricle non-refractory period, and the upper limit Q of the ventricle stimulation is used as the intensity of the stimulation pulse. The period from T3 to T4 is in the refractory periods of the ventricles RV and LV and the atria RA and LA, and a value R that is sufficiently larger relative to the respective upper limits P and Q is used as the intensity of the stimulation pulse. The period from T4 to T5 is in the non-refractory period of the atria and in the refractory period of the ventricles, and the upper limit P of the atrium stimulation is used as the intensity of the stimulation pulse. The period from T5 to T6 is in the non-refractory periods of the ventricles RV and LV and the atria RA and LA, and the smaller upper limit P of the two upper limits is used as the intensity of the stimulation pulse. The same procedure is repeated thereafter.

By doing so, it is possible to avoid stimulation of both the atria RA and LA and the ventricles RV and LV which would cause an adverse effect, which affords an advantage in that it is possible to perform sufficient nerve stimulation while reducing the adverse effect on the heart H.

What is claimed is:

1. A nerve stimulation apparatus comprising:
    a stimulation signal output unit configured to output a nerve stimulation signal;
    a cardiac event detector configured to detect a cardiac event; and
    a controller configured to control the stimulation signal output unit so as to output, in a non-refractory period, a nerve stimulation signal having a smaller intensity than that in a cardiac refractory period,
    wherein the cardiac refractory period is obtained on the basis of the cardiac event detected by the cardiac event detector, and
    wherein the controller is configured, in the non-refractory period, to compare a previous depolarization interval with a depolarization interval of interest, to determine a rate of change between the previous depolarization interval and the depolarization interval of interest, and to set an upper limit of an intensity of the nerve stimulation signal on the basis of the rate of change, and
    wherein the controller is configured to set an intensity of a following nerve stimulation signal larger than the upper limit of the intensity of the nerve stimulation signal when the rate of change is smaller than a predetermined value.

2. A nerve stimulation apparatus according to claim 1, wherein the intensity of the nerve stimulation signal is equal to energy per pulse signal that is output from the stimulation signal output unit.

3. A nerve stimulation apparatus according to claim 1, wherein the intensity of the nerve stimulation signal is equal to energy per unit time of the nerve stimulation signal that is output from the stimulation signal output unit.

4. A nerve stimulation apparatus according to claim 1, wherein the intensity of the nerve stimulation signal is equal to a total energy of the nerve stimulation signal that is output from the stimulation signal output unit.

5. A nerve stimulation apparatus according to claim 1, wherein the nerve stimulation signal that is output from the stimulation signal output unit in a non-refractory period has an intensity that does not stimulate the heart.

6. A nerve stimulation apparatus according to claim 5, wherein the nerve stimulation signal that is output from the stimulation signal output unit in the non-refractory period has an intensity that does not stimulate the atrium.

7. A nerve stimulation apparatus according to claim 5, wherein the nerve stimulation signal that is output from the stimulation signal output unit in the non-refractory period has the intensity that does not stimulate the ventricle.

8. A nerve stimulation apparatus according to claim 1, wherein the controller is configured to control the stimulation signal output unit such that the nerve stimulation signal that is output from the stimulation signal output unit in the non-refractory period has an intensity upper limit that does not stimulate the heart, and such that the nerve stimulation signal that is output from the stimulation signal output unit in the refractory period has an intensity larger than the upper limit.

9. A nerve stimulation apparatus according to claim 1, wherein the controller is configured to obtain a refractory period of the ventricle and a refractory period of the atrium as the cardiac refractory period and controls the stimulation signal output unit such that the nerve stimulation signal that is output from the stimulation signal output unit in the non-refractory period of the atrium has an intensity upper limit that does not stimulate the atrium, the nerve stimulation signal that is output from the stimulation signal output unit in the refractory period of the atrium and in the non-refractory period of the ventricle has an intensity upper limit that does not stimulate the ventricle, and the nerve stimulation signal that is output from the stimulation signal output unit in the refractory period of the atrium and in the refractory period of the ventricle has a larger intensity than the intensity upper limit that does not stimulate the ventricle.

* * * * *